(12) United States Patent
Demel

(10) Patent No.: US 9,414,988 B2
(45) Date of Patent: Aug. 16, 2016

(54) KIT COMPRISING A PACKAGING MATERIAL AND A SOLID PHARMACEUTICAL OR NUTRACEUTICAL PRODUCT CONTAINED IN THE PACKAGING MATERIAL

(75) Inventor: Peter Demel, Rheinfelden (DE)

(73) Assignee: SIEGFRIED LTD., Zofingen (CH)

( * ) Notice: Subject to any disclaimer, the term of this patent is extended or adjusted under 35 U.S.C. 154(b) by 293 days.

(21) Appl. No.: 14/240,848

(22) PCT Filed: Sep. 4, 2012

(86) PCT No.: PCT/EP2012/003684
§ 371 (c)(1),
(2), (4) Date: Feb. 25, 2014

(87) PCT Pub. No.: WO2013/034273
PCT Pub. Date: Mar. 14, 2013

(65) Prior Publication Data
US 2014/0190866 A1  Jul. 10, 2014

(30) Foreign Application Priority Data
Sep. 5, 2011 (EP) .................................. 11007164

(51) Int. Cl.
| | |
|---|---|
| A61J 1/03 | (2006.01) |
| B32B 27/08 | (2006.01) |
| B32B 27/34 | (2006.01) |
| B32B 27/36 | (2006.01) |
| B32B 27/38 | (2006.01) |
| A61K 31/138 | (2006.01) |
| A61K 31/225 | (2006.01) |
| A61K 31/245 | (2006.01) |
| A61K 31/4152 | (2006.01) |
| A61K 31/47 | (2006.01) |
| A61K 31/485 | (2006.01) |
| B65D 65/38 | (2006.01) |
| B65D 81/24 | (2006.01) |

(52) U.S. Cl.
CPC ................ *A61J 1/03* (2013.01); *A61K 31/138* (2013.01); *A61K 31/225* (2013.01); *A61K 31/245* (2013.01); *A61K 31/4152* (2013.01); *A61K 31/47* (2013.01); *A61K 31/485* (2013.01); *B32B 27/08* (2013.01); *B32B 27/34* (2013.01); *B32B 27/36* (2013.01); *B32B 27/38* (2013.01); *B32B 2250/02* (2013.01); *B32B 2250/24* (2013.01); *B32B 2439/40* (2013.01); *B32B 2439/60* (2013.01); *B32B 2439/70* (2013.01); *B32B 2439/80* (2013.01); *B65D 65/38* (2013.01); *B65D 81/24* (2013.01)

(58) Field of Classification Search
CPC ........... A61J 1/03; B32B 27/08; B32B 27/34; B32B 27/36; B32B 27/38; B32B 2250/02; B32B 2250/24; B32B 2439/40; B32B 2439/46; B32B 2439/60; B32B 2439/70; B32B 2439/80; B65D 65/38; B65D 81/24; A61K 31/138; A61K 31/225; A61K 31/245; A61K 31/4152; A61K 31/485
See application file for complete search history.

(56) References Cited

U.S. PATENT DOCUMENTS

| | | |
|---|---|---|
| 5,242,757 A | 9/1993 | Buisine et al. |
| 6,767,601 B2 | 7/2004 | Colombo |
| 2007/0117830 A1 | 5/2007 | Chapman et al. |
| 2009/0071855 A1 | 3/2009 | Bahuguna et al. |
| 2010/0268187 A1 | 10/2010 | Singla et al. |

FOREIGN PATENT DOCUMENTS

| | | |
|---|---|---|
| EP | 2 353 573 | 8/2011 |
| WO | WO 95/15992 A1 | 6/1995 |
| WO | WO 2009/019668 A2 | 2/2009 |

OTHER PUBLICATIONS

International Preliminary Report on Patentability issued in International Patent Application No. PCT/EP2012/003684 dated Mar. 12, 2014.
International Search Report issued in International Patent Application No. PCT/EP2012/003684 dated Jan. 8, 2013.

*Primary Examiner* — Michael C Miggins
(74) *Attorney, Agent, or Firm* — Oliff PLC

(57) ABSTRACT

A kit including a packaging material and a solid pharmaceutical or nutraceutical product, and in particular for a solid, opioid-based pharmaceutical product. The packaging material has an inner surface and an outer surface that avoids contamination of the product. At least that part of the inner surface, which is exposed to the pharmaceutical or nutraceutical product, is made of or covered with an inert material selected from the group made of polyamide, polyethylene terephthalate and epoxy resin-coated aluminium. The solid pharmaceutical or nutraceutical product is either a solid, opioid-based pharmaceutical product or is selected from the group made of acemetacin, amitriptyline, amobarbital, butalbital, carbachol, citric acid, dexmethylphenidate, fluoxetine, mephobarbital, metamizole, methadone, methylphenidate, methylphenobarbital, nicotine, nifedipine, oxprenolol, oxyconazole, pentobarbital, phenobarbital, phentermine, primidone, proparacaine, propoxyphene, secobarbital, selegiline, tetrahydropapaverine, trimethobenzamide, and mixtures thereof.

14 Claims, No Drawings

KIT COMPRISING A PACKAGING MATERIAL AND A SOLID PHARMACEUTICAL OR NUTRACEUTICAL PRODUCT CONTAINED IN THE PACKAGING MATERIAL

The present invention relates to a kit comprising a packaging material and a solid pharmaceutical or nutraceutical product contained in the packaging material.

The term "pharmaceutical product", as used throughout this application, refers to any chemical substance intended for use in medical diagnosis, cure, treatment or prevention of disease, both in humans and animals. It includes both the active agent (i.e. the chemical substance) in pure form, as well as in combination with any other active agent(s) and/or excipient(s).

Furthermore, the term "active agent", as used throughout this application, includes all forms of a pharmaceutically or nutraceutically active substance, including salts and complexes thereof.

The term "nutraceutical product", as used throughout this application, refers to a food or food product that provides health benefits. Examples of nutraceutical products are, for instance, dietary supplements, functional foods or medical foods. Again, these products may be intended for humans or animals. Furthermore, "nutraceutical products" includes both the active agent in pure form, as well as in combination with any other active agent(s), food and/or excipient(s).

The term "opioid-based pharmaceutical product", as used throughout this application, refers to a pharmaceutical product comprising one or more opioids or salts thereof.

Opioids are among the world's oldest known drugs and have long been used to treat acute pain, such as post-operative pain. They have also been found to be invaluable in palliative care to alleviate the severe, chronic, disabling pain of terminal conditions, such as cancer, and degenerative conditions, such as rheumatoid arthritis. Some of the most used opioid drugs include morphine, codeine, hydromorphone, naltrexone, and salts thereof.

Most opioid-based pharmaceutical products are in the form of solid crystals and are water soluble. They are traditionally stored in polyethylene bags or in glass containers.

It has recently been found that these polyethylene packaging materials lead to a contamination of the opioid-based pharmaceutical products. This contamination, which is in the form of small solid particles and is insoluble in water, seems to consist of polyethylene oligomers. The contamination is observed after transport and handling, as well as after unmoved storage.

Such a contamination of the pharmaceutical or nutraceutical product by the packaging material may affect its suitability for the intended use.

It is therefore an object of the present invention, to provide a packaging material for a solid pharmaceutical or nutraceutical product, and in particular for an opioid-based pharmaceutical product, which avoids a contamination of the pharmaceutical or nutraceutical product.

This problem is solved by the claimed kit and the method. Preferred embodiments are subject of the dependent claims.

The present invention features a kit comprising a packaging material and a solid pharmaceutical or nutraceutical product which is contained in the packaging material, the packaging material having an inner surface and an outer surface, characterized in that at least that part of the inner surface, which is exposed to the pharmaceutical or nutraceutical product, is made of or covered with an inert material selected from the group consisting of polyamide, polyethylene terephthalate and epoxy resin-coated aluminum. The solid pharmaceutical or nutraceutical product is either a solid, opioid-based pharmaceutical product or is selected from the group consisting of acemetacin, amitriptyline, amobarbital, butalbital, carbachol, citric acid, dexmethylphenidate, fluoxetine, mephobarbital, metamizole, methadone, methylphenidate, methylphenobarbital, nicotine, nifedipine, oxprenolol, oxyconazole, pentobarbital, phenobarbital, phentermine, primidone, proparacaine, propoxyphene, secobarbital, selegiline, tetrahydro-papaverine, trimethobenzamide, and mixtures thereof.

Throughout the present application, the pharmaceutical and nutraceutical products mentioned include the free active agents, e.g. an acid or a base, as well as the corresponding salts, hydrates, solvates and hydrates or solvates of salts.

Surprisingly, it has been found that if the inner surface of the packaging material is made of or covered with polyamide, polyethylene terephthalate or epoxy resin-coated aluminium, contamination of the pharmaceutical or nutraceutical product is completely avoided. Even upon prolonged heating or vigorous shaking of the packaged product, no contamination is observed. For this reason, the packaging material of the present invention is particularly well suited for solid products, which are intended for administration to a human or animal, such as pharmaceutical or nutraceutical products.

According to the present invention, the solid pharmaceutical or nutraceutical product is contained in the packaging material. The packaging material may have any form, three-dimensional shape and/or size suitable for packaging the pharmaceutical or nutraceutical product. Thus, the packaging material of the present invention is generally in the form of a "packaging" or "container".

The packaging material may further be open on one side such as a normal bag, basket or open box, re-closable by means of e.g. a re-closable lid or zipper, or it may be sealed without re-closable opening, thereby ensuring that the packaging material has not been opened after packing the product.

The packaging material of the present invention has an inner surface, which is facing the solid pharmaceutical or nutraceutical product and at least part of which is in direct contact with said product, and an outer surface, which is facing the external environment. In order to avoid the contamination of the stored product, at least that part of the inner surface, which is directly exposed to the product—i.e. may come into contact with the product—has to be made of or covered with the inert material.

In terms of the present invention, the "inner surface" is that surface of the packaging material which will face the interior of a three-dimensional structure formed by the packaging material. In a preferred embodiment, the inert material is polyamide, polyethylene terephthalate or epoxy resin-coated aluminium. In addition to fully avoiding contamination, these materials also allow for a very simple and straight forward preparation of the packaging material, which is easily brought into the desired shape by standard methods. Particularly preferred polyamides are PA6.6, PA6, and/or PA11. PA6.6 has the formula $(NH-(CH_2)_6-NH-CO-(CH_2)_4-CO]_n$ and is made from hexamethylenediamine and adipic acid. PA6 has the formula $[NH-(CH_2)_5-CO]_n$ and is made from ε-caprolactam. PA11 has the formula $[NH-(CH_2)_{10}-CO]_n$ and is made from 11-amino undecanoic acid.

In a preferred embodiment, the entire inner surface of the packaging material is made of or covered with the inert material. This allows for an even simpler production of the packaging material, as the entire inner surface can be treated in the same way. Furthermore, upon packaging the opioid-based pharmaceutical product, it is not necessary to pay extra attention to make sure that only that part of the inner surface, which is made of or covered with the inert material, can come in contact with the pharmaceutical product.

In a preferred embodiment, the inert material has a thickness of at least 5 μm, preferably of at least 10 μm, more preferably of at least 20 μm, and most preferably of about 30 μm. This allows for safe and contamination free packaging of the opioid-based pharmaceutical product, while not requiring excessive amounts of material.

Preferably, the thickness of the inert material is essentially the same in all areas of the packaging material. Alternatively, it is also possible that the thickness of the inert material is increased in those areas, which are subjected to elevated mechanical stress, such as a closing or buckling area.

In a preferred embodiment, the inner surface of the packaging material is made of polyamide and the outer surface is made of polyethylene. This combination of materials provides a suitable packaging of any size for the pharmaceutical or nutraceutical product, in addition to avoiding contamination of the product by the packaging material itself. Furthermore, such a material can be easily produced by standard methods generally used in the packaging industry and can be brought into any desired shape.

In a particularly preferred embodiment, the packaging material consists of an inner polyamide layer and an outer polyethylene layer and is preferably in the form of a foil, which is sealed to form a bag. In addition, the outer layer of this foil may be covered with a gas tight layer, such as an aluminium layer, in order to provide an air and gas tight packaging.

In a preferred embodiment, the packaging material of the present invention is in the form of a bag. Alternatively, it may also be in the form of a plastic bottle, a plastic hose or a coated metal container.

Further preferred forms of the packaging material of the present invention are any sorts of containers, boxes, cans or baskets, which have a rectangular, cylindrical or spherical form, or are shaped in form of a Platonic body, such as a tetrahedron, cube or hexahedron, octahedron, dodecahedron, icosahedron or other polygon. Further preferred forms of the packaging material are a bag in any three-dimensional shape, e.g. a pyramid bag, a bag-in-box packaging, an envelope or a tube.

The kit according to the present invention allows for safe and contamination free transport, storage and handling of the pharmaceutical or nutraceutical product.

In general, the kit according to the present invention may contain any solid chemical product, which is intended for administration to humans or animals. Basically for all chemical products, which are to be administered to a human or animal, independent of the intended form of administration, a contamination of the chemical product by the packaging material is undesirable.

Especially if the product is dose-sensitive, such as drug-like pharmaceuticals, it is preferred that the product is sealed, optionally under sterile conditions, into the packaging material. That way, it is possible to supply the kit of the present invention comprising a specific dose of the pharmaceutical or nutraceutical product provided in the packaging material. Without breaking the sealed packing material, no product can be added or removed, thus an intact packaging material can serve as guarantee that the amount and/or quality of contained product has not been changed after packaging and sealing.

In a preferred embodiment, the solid pharmaceutical or nutraceutical product is water soluble. In terms of the present invention, "water soluble" means that a major part of the product is dissolvable in water at room temperature (about 18 to 26° C.). Many of these products are dissolved in water prior to administration to a patient. It is therefore particularly important, that they do not contain any water insoluble contaminations, such as the ones observed for polyethylene bags. Thanks to the packaging material of the present invention, this problem is completely avoided. According to a further preferred embodiment, the packaging material is in form of a watertight container, into which a liquid, such as water, can be filled in order to dissolve the contained product.

It is further preferred that the packaging material comprises an inlet through which a liquid can be transferred. For example, the solid product may be sealed in a packaging material in form of an infusion container. Such an infusion container may be flexible—in form of an infusion bag—or it may also have a more or less rigid three-dimensional structure such as an infusion bottle. It is further provided with an outlet connectable to a tube for attaching the infusion to a patient and an inlet through which a liquid can be transferred into the infusion container in order to dissolve the contained product.

In the above described case, it is further preferred that a liquid, e.g. water, can be transferred into the infusion container in a sterile manner. This may be achieved, for instance, by transferring the liquid into the container through a one-way inlet that allows for sterile transfer of a liquid into the bag, but does not allow the extraction of material from the container. The concentration of the product dissolved in the liquid solution can easily be set by the amount of liquid added into the container. After dissolving the product, the infusion container can directly be fixed on an infusion stand and connected via a tube to a patient for infusing the dissolved product.

However, also other solid pharmaceutical or nutraceutical products, which are intended for other forms of administration, such as tablets, capsules, injections or patches, may be contained in the packaging material of the present invention. The packaging material of the present invention is particularly advantageous for "problematic" pharmaceutical products, i.e. for those products, which are known to put more than average strain on the packaging material. Such an elevated strain may be due to a particular particle size, crystal structure (due to different polymorphs) or hardness of the product, for instance.

In a preferred embodiment, the solid pharmaceutical or nutraceutical product has a particle size of about 10 to 1200 μm. This particle size largely depends on the nature of the pharmaceutical or nutraceutical product; typical particle sizes are, for instance: 10 to 1200 μm for buprenorphine; less than 200 μm, more preferably less than 100 μm for hydromorphone; less than 150 μm, more preferably about 50 to 90 μm for naltrexone; less than 200 μm, more preferably less than 100 μm for morphine sulphate; and less than 20 μm, more preferably less than 15 μm for micronized morphine sulphate.

Throughout this application, particle sizes are indicated as the d(90) value. This means that 90% of the particles are smaller than the indicated value. Therefore, as an example, if the particle size of hydromorphone is indicated as less than 100 μm, this means that the d(90) value is 100 μm and thus that 90% of the hydromorphone particles are smaller than 100 μm.

Various Methods for measuring the particle size are known to a person skilled in the art, such as Sieve analysis, Malvern, Low-Angle-Laser-Light-Scattering, Dynamic Light Scattering, Laser-Diffraction, Spatial Filter Velocimetry, Image Analysis or Micromeritics, for instance.

In a preferred embodiment, the solid pharmaceutical or nutraceutical product is crystalline.

In a preferred embodiment, the kit comprises a solid, opioid-based pharmaceutical product, which is contained in the packaging material. It has been found that especially opioid-based pharmaceutical products tend to be contaminated by the conventionally used polyethylene-based packaging materials. It is therefore particularly advantageous to use the packaging material of the present invention for opioid-based pharmaceutical products.

In a preferred embodiment, the solid, opioid-based pharmaceutical product comprises an opioid, which is selected from the group consisting of buprenorphine, codeine, hydrocodone, hydromorphone, methylnaltrexone, morphine, naloxone, naltrexone, oxycodone, oxymorphone, and mixtures thereof. As mentioned above, the pharmaceutical and nutraceutical products mentioned include the free active agents, e.g. an acid or a base, as well as the corresponding salts, hydrates, solvates and hydrates or solvates of salts.

Furthermore, these products may be in any known polymorphic form or a mixture thereof.

More preferred, the solid, opioid-based pharmaceutical product comprises buprenorphine, buprenorphine hydrochloride, codeine phosphate, hydrocodone bitartrate, hydromorphone hydrochloride, methylnaltrexone bromide, morphine sulphate, naloxone, naloxone hydrochloride, naltrexone, naltrexone hydrochloride, oxycodone hydrochloride, and/or oxymorphone hydrochloride. It has been found that the packaging material of the present invention is particularly advantageous for these opioid-based products.

In a further preferred embodiment, the kit of the present invention comprises a pharmaceutical or nutraceutical product, which is selected from the group consisting of acemetacin, amitriptyline, amobarbital, butalbital, carbachol, citric acid, dexmethylphenidate, fluoxetine, mephobarbital, metamizole, methadone, methylphenidate, methylphenobarbital, nicotine, nifedipine, oxprenolol, oxyconazole, pentobarbital, phenobarbital, phentermine, primidone, proparacaine, propoxyphene, secobarbital, selegiline, tetrahydropapaverine, trimethobenzamide, and mixtures thereof.

More preferred, the solid pharmaceutical or nutraceutical product comprises acemetacin, amitriptyline hydrochloride, butalbital, carbachol, citric acid, dexmethylphenidate hydrochloride, fluoxetine hydrochloride, methadone, methadone hydrochloride, methylphenidate, methylphenidate hydrochloride, methylphenobarbital, mephobarbital, nicotine bitartrate, nifedipine, oxyconazole nitrate, oxprenolol hydrochloride, phentermine, phentermine hydrochloride, primidone, proparacaine hydrochloride, propoxyphene hydrochloride, propoxyphene napsylate, selegiline hydrochloride, sodium amobarbital, sodium metamizole, sodium pentobarbital, sodium phenobarbital, sodium secobarbital, trimethobenzamide hydrochloride, and/or (R)-tetrahydropapaverine. It has been found that the packaging material of the present invention is particularly advantageous for these pharmaceutical or nutraceutical products.

In a further aspect, the present invention also refers to the use of the packaging material described above for the packaging of a solid pharmaceutical or nutraceutical product, and in particular of a solid, opioid-based pharmaceutical product. Preferably, the packaging material is used for enclosing the solid pharmaceutical or nutraceutical product during transport, storage, and/or handling.

Preferred embodiments of the use of the packaging material according to the present invention comprise all preferred embodiments of the packaging material and all preferred solid pharmaceutical or nutraceutical products described above for the kit.

The present invention is further illustrated by way of the following, non-limiting examples:

Abbreviations:
PE polyethylene
Al aluminium
PTFE polytetrafluoroethylene
PET polyethylene terephthalate
PETP polyethylene terephthalate
LDPE low density polyethylene
PP polypropylene
PA polyamide
PA11 polyamide polymer based on 11-amino undecanoic acid
OPA polyamide polymer
PVC polyvinyl chloride
FTU Formazin turbidity unit (also called FTE)
RH relative humidity
Determination of Cloudiness of Hydromorphone Hydrochloride For the determination of cloudiness, hydromorphone hydrochloride was dissolved in water (5 wt %) and the turbidity was determined in a turbimeter based on light scattering.

EXAMPLE 1

Unmoved Storage of Hydromorphone Hydrochloride

Samples of hydromorphone hydrochloride (about 10 to 20 g) were stored in different packaging materials at a temperature of 50° C. for 26 days. During this period, mechanical impact on the packaged samples was avoided as far as possible. The cloudiness was determined as described above.

The following packaging materials have been tested:

| # | Packaging Material | Cloudiness [FTU] | Difference from Intial Cloudiness [FTU] |
|---|---|---|---|
| 0 | Initial cloudiness | 1.5 | — |
| 1 | "Purell" PE bag, "standard quality" (Vinora Petroblast) | 2.4 | 0.9 |
| 2 | Al bottle (Tournaire S.A., France) | 1.6 | 0.1 |
| 3 | PTFE bag (Lanz Anliker) | 2.4 | 0.9 |
| 4 | PET bottle (Pohli GmbH) | 1.7 | 0.2 |
| 5 | Composite bag PE/PETP/Al (Früh); large black bag | 2.7 | 1.2 |
| 6 | Composite bag PE/PETP/Al (Früh); small silver bag | 2.9 | 1.4 |
| 7 | "Purell" PE bag, "higher quality" (Vinora Petroblast) | 2.2 | 0.7 |
| 8 | PE bag "BK CleanFlex ®" with special PE film (Mat. No. 45123.0187/402696.0001) | 2.0 | 0.5 |
| 9 | PE bag "BK CleanFlex ®" with 100% LDPE film (Mat. No. 9824.0001) | 2.1 | 0.6 |
| 10 | PE bag "BK CleanFlex ®" with 100% LDPE film (Mat. No. 1631.0031/400294.003) | 2.8 | 1.3 |
| 11 | PE foil BK CleanFlex ® with 100% PP film (Mat. No. 9820.0273) | 2.3 | 0.8 |
| 12 | PP*/PA11 composite foil, 110/60 (Stanipac) | 2.1 | 0.6 |
| 13 | PP/PA11* composite foil, 110/60 (Stanipac) | 2.0 | 0.5 |
| 14 | PET*/PE composite foil, 12/50 (Stanipac) | 1.8 | 0.3 |

-continued

| # | Packaging Material | Cloudiness [FTU] | Difference from Intial Cloudiness [FTU] |
|---|---|---|---|
| 15 | PET/PE* composite foil, 12/50 (Stanipac) | 2.1 | 0.6 |
| 16 | PA/PE* composite foil, 30/70 (Stanipac) | 2.25 | 0.75 |
| 17 | PA*/PE composite foil, 30/70 (Stanipac) | 1.3 | −0.2 |
| 18 | OPA/PE* composite foil, 15/60 (Stanipac) | 2.2 | 0.7 |
| 19 | OPA*/PE composite foil, 15/60 (Stanipac) | 2.2 | 0.7 |

*In the case of composite bags/foils, the component facing the hydromorphone hydrochloride is underlined.

In summary, the use of packaging materials with PE/PP and PTFE on the inner surface lead to an increase of cloudiness of about 0.84 FTU and 0.9 FTU, respectively (comparative examples).

For PET (0.23 FTU), PA (−0.2 FTU) and Al (0.1 FTU), on the other hand, only a minor increase or even a decrease in cloudiness was observed (packaging materials according to the present invention). A variation of up to ±0.2 is generally regarded as a constant value in the field.

EXAMPLE 2

Storage of Hydromorphone Hydrochloride with Mechanical Impact

Samples of hydromorphone hydrochloride were stored in different packaging materials at room temperature for two hours. During this period, the packaged samples were subjected to mechanical impact in a Turbula® shaker-mixer (mixing in all three dimensions) at 46 rpm. Bags and foils had to be placed into a surrounding glass bottle due to the arrangement of the shaker-mixer. The cloudiness was determined as described above.

The following packaging materials have been tested:

| # | Packaging Material | Cloudiness [FTU] | Difference from Initial Cloudiness [FTU] |
|---|---|---|---|
| 20 | Initial cloudiness | 1.2 | — |
| 21 | "Purell" PE bag, "standard quality" (Vinora Petroblast) | 1.8 | 0.6 |
| 22 | PET*/PE composite foil, 12/50 (Stanipac) | 1.3 | 0.1 |
| 23 | PA*/PE composite foil, 30/70 (Stanipac) | 1.3 | 0.1 |

*In the case of composite bags/foils, the component facing the hydromorphone hydrochloride is underlined.

Thus, almost no increase in cloudiness was observed for PET and PA.

For PE, on the other hand, a considerable increase in cloudiness was measured.

EXAMPLE 3

Unmoved Storage of Naltrexone Hydrochloride at Elevated Temperature and Humidity An appropriate amount of naltrexone hydrochloride was placed into the primary packaging material to be investigated (see table below), which was in turn placed into an appropriate secondary packaging material. The so packaged naltrexone hydrochloride was then placed in stability chambers at temperatures between 25° C. and 40° C. and relative humidities between 60% and 75%.

After the given amount of time, appropriate aliquots of naltrexone hydrochloride were taken from the above samples and analyzed for cloudiness of solution. For this purpose, 2 wt % solutions of naltrexone hydrochloride in Milli-Q water were prepared and investigated in a turbidimeter (e.g. Hack turbidimeter) while applying the FTU-scale (Formazine turbidity unit).

The following packaging materials have been tested:

| # | Lot-No. Naltrexone HCl | Primary Packaging Material | Conditions | Cloudiness [FTU] | Difference from Initial Cloudiness [FTU] |
|---|---|---|---|---|---|
| 24 | 0916L698 | PE[1] | initial cloudiness (t0) | 1.2 | n/a |
| 25 | | | 3 months, 25° C., 60% RH | 1.3 | 0.1 |
| 26 | | | 3 months, 30° C., 65% RH | 1.7 | 0.5 |
| 27 | | | 3 months, 40° C., 75% RH | 3.9 | 2.7 |
| 28 | | | 6 months, 25° C., 60% RH | 3.3 | 2.1 |
| 29 | | | 6 months, 30° C., 65% RH | 6.8 | 4.6 |
| 30 | | | 6 months, 40° C., 75% RH | 7.0 | 5.8 |
| 31 | 0914L009 | PE[1] | initial cloudiness (t0) | 1.6 | n/a |
| 32 | | | 3 months, 25° C., 60% RH | 3.8 | 2.2 |
| 33 | | | 3 months, 30° C., 65% RH | 3.9 | 2.3 |
| 34 | | | 3 months, 40° C., 75% RH | 5.0 | 3.4 |
| 35 | 0916L700 | PA[2] | initial cloudiness (t0) | 1.1 | n/a |
| 36 | | | 3 months, 25° C., 60% RH | 1.2 | 0.1 |
| 37 | | | 3 months, 30° C., 65% RH | 1.1 | 0.0 |
| 38 | | | 3 months, 40° C., 75% RH | 1.4 | 0.3 |
| 39 | 0916L700 | Epoxy-resin coated Al-bottles[2] | initial cloudiness (t0) | 1.1 | n/a |
| 40 | | | 3 months, 25° C., 60% RH | 1.7 | 0.6 |
| 41 | | | 3 months, 30° C., 65% RH | 1.7 | 0.6 |

| # | Lot-No. Naltrexone HCl | Primary Packaging Material | Conditions | Cloudiness [FTU] | Difference from Initial Cloudiness [FTU] |
|---|---|---|---|---|---|
| 42 | | | 3 months, 40° C., 75% RH | 1.3 | 0.2 |

[1]Stability protocol SP-QC-10-002;
[2]SP-QC-10-047;
[3]SP-QC-10-016.

From the above results, it can be clearly concluded that (compared with PE) the alternative packaging materials PA and epoxy-resin coated aluminium-bottles are preferable packaging materials (less increase of cloudiness).

EXAMPLE 4

Screening of Water-Soluble Substances in a Primary Packaging Abrasion Testing Device (P²AT-Device)

10 g of the substance 1 to be investigated was placed on a foil 2 of an appropriate packaging material, which itself was placed a glass-ware baseplate 3 (see FIG. 1). The area of packaging material 2 to be tested was limited to 100 cm², which is defined by the size of a Viton O-ring (not shown) sealed top cover 4 (with an inner diameter of 11.28 cm). A glass plate 5 of approx. 240 g weight with a diameter of 11.0 cm was placed on top of the substance 1 and the Viton O-ring sealed top cover 4 was arranged on top of the device. The whole system was then closed with an external bracket (not shown).

The test device (set-up as describe above) was placed on a laboratory shaker (not shown) and agitated for 6 hours at approx. 380 rpm. The top cover 4 and the O-ring were removed. Residual substance 1 sticking to the glass-plate 5 was removed using a spatula and the substance 1 to be tested was transferred into a clean brown-glass screw-bottle and weighed. The investigated packaging material-foil was rinsed with deionized water, dried, visually inspected for abrasion.

The substance to be investigated was then dissolved in water (or an appropriate mixture of water and a water-miscible co-solvent) and analyzed for turbidity/cloudiness using a turbidimeter (e.g. Hack turbidimeter) using the FTU-scale (formazine turbidity unit). Relevant parameters for the analytical procedure are given in the footnotes of the table below.

The following substances have been tested:

| # | Substance | Packaging Material | Cloudiness [FTU][15] | Difference from initial cloudiness [FTU] |
|---|---|---|---|---|
| 43 | Hydromorphone HCl[1] (sample 1) | initial cloudiness | 1.45 | n/a |
| 44 | | PE[2] | 30 | 28.55 |
| 45 | | PA[3] | 2.15 | 2.5 |
| 46 | Hydromorphone HCl[1] (sample 2) | initial cloudiness | 1.1 | n/a |
| 47 | | PP[17] | 9 | 7.9 |
| 48 | | PE-2[18] | 18 | 16.9 |
| 49 | | OPA/PE[19] | 2.3 | 1.2 |
| 50 | | PA11/PP[20] | 2.4 | 1.3 |
| 51 | | PET/PE[21] | 3.6 | 2.5 |
| 52 | Naloxone HCl[4] (sample 1) | initial cloudiness | 0.85 | n/a |
| 53 | | PE[2] | 1.35 | 0.5 |
| 53 | | PA[3] | 0.95 | 0.1 |
| 55 | Naloxone HCl[1] (sample 2) | initial cloudiness | 0.4 | n/a |
| 56 | | PP[17] | 1.7 | 1.3 |
| 57 | | PE-2[18] | 8.4 | 8.0 |
| 58 | | OPA/PE[19] | 1.1 | 0.7 |
| 59 | | PET/PE[21] | 0.8 | 0.4 |
| 60 | Naltrexon HCl[5] | initial cloudiness | 1.1 | n/a |
| 61 | | PA[3] | 1.2 | 0.7 |
| 62 | | PE-2[18] | 2.3 | 1.8 |
| 63 | | OPA/PE[19] | 1.4 | 0.9 |
| 64 | | PA11/PP[20] | 1.4 | 0.9 |
| 65 | | PET/PE[21] | 1.2 | 0.7 |
| 66 | | PA/PE[22] | 1.0 | 0.5 |
| 67 | Morphine Sulphate[6] | initial cloudiness | 0.65 | n/a |
| 68 | | PE[2] | 2.0 | 1.35 |
| 69 | | PA[3] | 1.0 | 0.35 |
| 70 | Oxycodone HCl[7] | initial cloudiness | 0.35 | n/a |
| 71 | | PE[2] | 0.6 | 0.25 |
| 72 | | PA[3] | 0.5 | 0.1 |
| 73 | Sodium Metamizole (sample 1) | initial cloudiness | 0.7 | n/a |
| 74 | | PE[2] | 24.5 | 23.8 |
| 75 | | PA[3] | 0.8 | 0.1 |
| 76 | Sodium Metamizole (sample 2) | initial cloudiness | 0.4 | n/a |
| 77 | | PP[17] | 1.0 | 0.6 |
| 78 | | PE-2[18] | 3.6 | 3.2 |
| 79 | | OPA/PE[19] | 0.7 | 0.3 |
| 80 | | PET/PE[21] | 0.6 | 0.2 |
| 81 | | PA/PE[22] | 0.6 | 0.2 |
| 82 | Fluoxetine HCl[9] (sample 1) | initial cloudiness | 0.2 | n/a |
| 83 | | PE[2] | 2.25 | 2.05 |
| 84 | | PA[3] | 0.3 | 0.1 |
| 85 | Fluoxetine HCl[9] (sample 2) | initial cloudiness | 0.2 | n/a |
| 86 | | PE-2[18] | 4.8 | 4.6 |
| 87 | | OPA/PE[19] | 0.3 | 0.1 |
| 88 | | PA11/PP[20] | 0.3 | 0.1 |
| 89 | | PET/PE[21] | 0.3 | 0.1 |
| 90 | | PA/PE[22] | 0.4 | 0.2 |
| 91 | Citric acid[11] (sample 1) | initial cloudiness | 0.4 | n/a |
| 92 | | PE[2] | 4.7 | 5.3 |
| 93 | | PA[3] | 2.05 | 1.65 |
| 94 | Citric acid[11] (sample 2) | initial cloudiness | 0.3 | n/a |
| 95 | | PP[17] | 4.5 | 4.2 |
| 96 | | PE-2[18] | 6.5 | 6.2 |
| 97 | | OPA/PE[19] | 1.7 | 1.4 |
| 98 | | PA11/PP[20] | 3.1 | 2.8 |
| 99 | | PET/PE[21] | 2.0 | 1.7 |
| 100 | | PA/PE[22] | 2.2 | 1.9 |
| 101 | Oxprenolol HCl[12] (sample 1) | initial cloudiness | 0.65 | n/a |
| 102 | | PE[2] | 1.45 | 0.8 |
| 103 | | PA[3] | 0.75 | 0.1 |
| 104 | Oxprenolol HCl[12] (sample 2) | initial cloudiness | 0.3 | n/a |
| 105 | | PE-2[18] | 3.2 | 2.9 |
| 106 | | OPA/PE[19] | 1.2 | 0.9 |
| 107 | Proparacaine HCl[13] (sample 1) | initial cloudiness | 1.6 | n/a |
| 108 | | PE[2] | 6.6 | 5.0 |
| 109 | | PA[3] | 1.55 | −0.05 |
| 110 | Proparacaine HCl[13] (sample 2) | initial cloudiness | 1.5 | n/a |
| 111 | | OPA/PE[19] | 2.0 | 0.5 |
| 112 | | PA/PE[22] | 1.9 | 0.4 |

-continued

| # | Substance | Packaging Material | Cloudiness [FTU][15] | Difference from initial cloudiness [FTU] |
|---|---|---|---|---|
| 113 | (R)-Tetrahydro-papaverine[14] | initial cloudiness | 1.6 | n/a |
| 114 | | PE[2] | 20 | 18.4 |
| 115 | | PA[3] | 1.8 | 0.2 |

[1]Analysis: 5 weight % in Milli Q-water;
[2]PE = PE-bag "Purell, standard-quality", Vinora Petroplast, Siegfried-Mat-No. 409667, Lot-No. 1050%001;
[3]Mat-No. 409608, Lot-No. 1044%003;
[4]Analysis: 2 weight % in Milli Q-water;
[5]Analysis: 2 weight % in Milli Q-water;
[6]Analysis: 2 weight % in Milli Q-water;
[7]Analysis: 2 weight % in Milli Q-water;
[8]Analysis: 5 weight % in Milli Q-water;
[9]Analysis: 2 weight % in Milli Q-water/Methanol 15/85;
[10]Analysis: 2 weight % in Milli Q-water;
[11]Analysis: 5 weight % in Milli Q-water;
[12]Analysis: 5 weight % in Milli Q-water;
[13]Analysis: 5 weight % in Milli Q-water;
[14]Analysis: 10 weight % in Milli Q-water;
[15]average of two independent sample preparations;
[16]difference of average value of two different sample preparations from the experiment vs. the initial cloudiness
[17]PP = PP-bag "BK CleanFlex ®", Mat. No. 9820.0273;
[18]PE-2 = PE-bag "BK CleanFlex ®" with 100% LDPE film (Mat. No. 1631.0031/400294.003);
[19]OPA/PE = OPA[23]/PE composite foil, 15/60 μm (Stanipac);
[20]PA11/PP = PA11[23]/PP composite foil, 60/110 μm (Stanipac);
[21]PET/PE = PET[23]/PE composite foil, 12/50 μm (Stanipac);
[22]PA/PE = PA[23]/PE composite foil, 30/70 μm (Stanipac);
[23]underlined material = contact surface.

From the above results, it can be clearly concluded that, compared to several types of thermoplasts, such as different types of PE or PP, the alternative packaging materials of different PA or PET types, either as single foil or as composite foil, show less increase of cloudiness.

The invention claimed is:

1. Kit comprising a packaging material and a solid pharmaceutical or nutraceutical product contained in the packaging material, the packaging material having an inner surface and an outer surface, wherein
at least a part of the inner surface, which is exposed to the pharmaceutical or nutraceutical product, is made of or covered with an inert material selected from the group consisting of polyamide, polyethylene terephthalate and epoxy resin-coated aluminium, and
the solid pharmaceutical or nutraceutical product is either a solid, opioid-based pharmaceutical product or is selected from the group consisting of acemetacin, amitriptyline, amobarbital, butalbital, carbachol, citric acid, dexmethylphenidate, fluoxetine, mephobarbital, metamizole, methadone, methylphenidate, methylphenobarbital, nicotine, nifedipine, oxprenolol, oxyconazole, pentobarbital, phenobarbital, phentermine, primidone, proparacaine, propoxyphene, secobarbital, selegiline, tetrahydropapaverine, trimethobenzamide, and mixtures thereof.

2. Kit comprising a packaging material and a solid pharmaceutical or nutraceutical product contained in the packaging material, the packaging material having an inner surface and an outer surface, wherein
at least a part of the inner surface, which is exposed to the pharmaceutical or nutraceutical product, is made of or covered with an inert material selected from the group consisting of polyamide, polyethylene terephthalate and epoxy resin-coated aluminium, and
the solid pharmaceutical or nutraceutical product comprises acemetacin, amitriptyline hydrochloride, butalbital, carbachol, citric acid, dexmethylphenidate hydrochloride, fluoxetine hydrochloride, methadone, methadone hydrochloride, methylphenidate, methylphenidate hydrochloride, methylphenobarbital, mephobarbital, nicotine bitartrate, nifedipine, oxyconazole nitrate, oxprenolol hydrochloride, phentermine, phentermine hydrochloride, primidone, proparacaine hydrochloride, propoxyphene hydrochloride, propoxyphene napsylate, selegiline hydrochloride, sodium amobarbital, sodium metamizole, sodium pentobarbital, sodium phenobarbital, sodium secobarbital, trimethobenzamide hydrochloride, and/or (R)-tetrahydropapaverine.

3. Kit according to claim 1, wherein the inert material is PA6.6, PA6 and/or PAH11.

4. Kit according to claim 1, wherein the entire inner surface of the packaging material is made of or covered with the inert material.

5. Kit according to claim 1, wherein the inert material has a thickness of at least 5 μm.

6. Kit according to claim 1, wherein the inner surface of the packaging material is made of polyamide and the outer surface is made of polyethylene.

7. Kit according to claim 1 wherein the packaging material has a three-dimensional form or shape.

8. Kit according to claim 1 wherein the packaging material is in the form of
a bottle,
a screw cap bottle,
a bag,
a box,
a bag-in-box packaging,
a basket,
a can,
an envelope,
a tube,
a container, or
an infusion container.

9. Kit according to claim 1 wherein the pharmaceutical or nutraceutical product is sealed into the packaging material.

10. Kit according to claim 1, wherein the solid, opioid-based pharmaceutical product comprises an opioid, which is selected from the group consisting of buprenorphine, codeine, hydrocodone, hydromorphone, methylnaltrexone, morphine, naloxone, naltrexone, oxycodone, oxymorphone, and mixtures thereof.

11. Kit according to claim 1, wherein the solid, opioid-based pharmaceutical product comprises buprenorphine, buprenorphine hydrochloride, codeine phosphate, hydrocodone bitartrate, hydromorphone hydrochloride, methylnaltrexone bromide, morphine sulphate, naloxone, naloxone hydrochloride, naltrexone, naltrexone hydrochloride, oxycodone hydrochloride, and/or oxymorphone hydrochloride.

12. A method of packaging a solid pharmaceutical or nutraceutical product for transport, storage and/or handling, the method comprising:
packaging a solid pharmaceutical or nutraceutical product in a packaging material, the packaging material having an inner surface and an outer surface, wherein
at least a part of the inner surface, which is exposed to the pharmaceutical or nutraceutical product, is made of or covered with an inert material selected from the group consisting of polyamide, polyethylene terephthalate and epoxy resin-coated aluminium, and the solid pharmaceutical or nutraceutical product is either a solid, opioid-based pharmaceutical product or is selected from the group consisting of acemetacin, amitriptyline, amobarbital, butalbital, carbachol, citric acid, dexmethylphenidate, fluoxetine, mephobarbital, metamizole, methadone, methylphenidate, methylphenobarbital, nicotine, nifedipine, oxprenolol, oxyconazole, pentobarbital, phenobarbital, phentermine, primidone, proparacaine, propoxyphene, secobarbital, selegiline, tetrahydropapaverine, trimethobenzamide, and mixtures thereof.

13. The method according to claim 12, wherein the solid, opioid-based pharmaceutical product comprises an opioid, which is selected from the group consisting of buprenorphine, codeine, hydrocodone, methylnaltrexone, morphine, hydromorphone, naloxone, naltrexone, oxycodone, oxymorphone, and mixtures thereof.

14. The method according to claim 12, wherein the solid, opioid-based pharmaceutical product comprises buprenorphine, buprenorphine hydrochloride, codeine phosphate, hydrocodone bitartrate, hydromorphone hydrochloride, methylnaltrexone bromide, morphine sulphate, naloxone, naloxone hydrochloride, naltrexone, naltrexone hydrochloride, oxycodone hydrochloride, and/oxymorphone hydrochloride.

* * * * *